US010578541B2

(12) United States Patent
Jooris et al.

(10) Patent No.: US 10,578,541 B2
(45) **Date of Patent: *Mar. 3, 2020**

(54) FLOW CYTOMETER WITH DIGITAL HOLOGRAPHIC MICROSCOPE

(71) Applicant: OVIZIO IMAGING SYSTEMS NV/SA, Brussels (BE)

(72) Inventors: Serge Jooris, Brussels (BE); Philip Mathuis, Brussels (BE)

(73) Assignee: Ovizio Imaging Systems NV/SA, Brussels (BE)

( * ) Notice: Subject to any disclaimer, the term of this patent is extended or adjusted under 35 U.S.C. 154(b) by 626 days.

This patent is subject to a terminal disclaimer.

(21) Appl. No.: 14/378,234

(22) PCT Filed: Feb. 3, 2013

(86) PCT No.: PCT/EP2013/052852
§ 371 (c)(1),
(2) Date: Aug. 12, 2014

(87) PCT Pub. No.: WO2013/120886
PCT Pub. Date: Aug. 22, 2013

(65) Prior Publication Data

US 2015/0056607 A1 Feb. 26, 2015

(30) Foreign Application Priority Data

Feb. 13, 2012 (EP) .................................... 12155139

(51) Int. Cl.
*G01N 15/14* (2006.01)
*G03H 1/04* (2006.01)
(Continued)

(52) U.S. Cl.
CPC ..... *G01N 15/1434* (2013.01); *G01N 15/1404* (2013.01); *G01N 21/6486* (2013.01);
(Continued)

(58) Field of Classification Search
CPC ........... G03H 1/0443; G03H 2001/005; G03H 1/0005; G03H 2001/0033; G01N 15/1404;
(Continued)

(56) References Cited

U.S. PATENT DOCUMENTS 4,786,594 A 11/1988 Khanna et al.
5,089,416 A * 2/1992 Schwartz ........... G01N 15/1012 356/243.2
(Continued)

FOREIGN PATENT DOCUMENTS

CN 202 808 799 3/2013
EP 0479231 A1 4/1992
(Continued)

OTHER PUBLICATIONS

Mihailescu M et al. "Microchannel-pinhole parameters investigation for cells visualization in holographic microscopy", Semiconductor Conference (CAS), 2011 International, IEEE pp. 75-78, XP032069149, DOI: 10.1109/SMICND.2011.6095718 ISBN: 978-1-61284-173-1. Published Oct. 17, 2011.
(Continued)

*Primary Examiner* — Gailene Gabel
(74) *Attorney, Agent, or Firm* — Knobbe, Martens, Olson & Bear, LLP

(57) ABSTRACT

The current invention concerns a flow cytometric system and method for observing, analyzing and/or separating objects in a liquid sample, comprising a digital holographic microscope (DHM) and at least one fluidic system, whereby the DHM comprises illumination means, an interferometric system and digital recording means, whereby the fluidic system is capable of guiding said objects through an illumination beam of the illumination means of said DHM, whereby the fluidic system comprises a mechanism for
(Continued)

inducing a liquid sample stream through the fluidic system, whereby preferably the fluidic system comprises a stream size controlling device for controlling the transverse dimensions of a liquid sample stream inside said fluidic system, preferably said stream size controlling device is capable of lining up the objects one-by-one or multiple objects at a time in said liquid sample stream.

18 Claims, 5 Drawing Sheets

(51) Int. Cl.
*G01N 21/64* (2006.01)
*G03H 1/00* (2006.01)
*G01N 15/10* (2006.01)

(52) U.S. Cl.
CPC ......... *G03H 1/0005* (2013.01); *G03H 1/0443* (2013.01); *G01N 15/1459* (2013.01); *G01N 2015/1006* (2013.01); *G01N 2015/1415* (2013.01); *G01N 2015/1445* (2013.01); *G03H 2001/005* (2013.01); *G03H 2001/0033* (2013.01)

(58) Field of Classification Search
CPC ....... G01N 15/1434; G01N 2015/1415; G01N 2015/1006; G01N 15/1459; G01N 2015/1445; G01N 21/6486
See application file for complete search history.

(56) References Cited

U.S. PATENT DOCUMENTS

| | | | | |
|---|---|---|---|---|
| 5,243,409 | A | 9/1993 | Sagner | |
| 5,256,571 | A | 10/1993 | Hurley et al. | |
| 5,495,333 | A * | 2/1996 | Konda | G01N 15/1459 250/574 |
| 6,249,345 | B1 | 6/2001 | Kraack | |
| 6,327,377 | B1 | 12/2001 | Rutenberg | |
| 6,361,934 | B1 | 3/2002 | Acton | |
| 6,394,966 | B1 | 5/2002 | Gill | |
| 6,651,008 | B1 | 11/2003 | Vaisberg et al. | |
| 6,809,862 | B2 | 10/2004 | Behnsen et al. | |
| 6,924,094 | B1 | 8/2005 | Gingeras et al. | |
| 6,954,667 | B2 | 10/2005 | Treado | |
| 7,009,700 | B2 | 3/2006 | Dubois et al. | |
| 7,286,222 | B2 | 10/2007 | Gardner | |
| 7,616,320 | B2 | 11/2009 | Javidi et al. | |
| 8,599,383 | B2 | 12/2013 | Teitell | |
| 9,569,664 | B2 | 2/2017 | Judkewitz | |
| 9,675,974 | B2 | 6/2017 | Jooris et al. | |
| 9,684,281 | B2 | 6/2017 | Mathuis et al. | |
| 9,846,151 | B2 * | 12/2017 | Magniette | A61B 10/0291 |
| 2002/0064328 | A1 | 5/2002 | Neuberger | |
| 2002/0106119 | A1 | 8/2002 | Foran | |
| 2002/0164063 | A1 | 11/2002 | Heckman | |
| 2003/0113832 | A1 | 6/2003 | Lauf | |
| 2003/0199649 | A1 | 10/2003 | Orbison et al. | |
| 2005/0036181 | A1 | 2/2005 | Marquet et al. | |
| 2005/0272103 | A1 | 12/2005 | Chen | |
| 2006/0014239 | A1 | 1/2006 | Luttmann et al. | |
| 2006/0088814 | A1 | 4/2006 | Hecht et al. | |
| 2006/0132799 | A1 * | 6/2006 | Dubois | G01N 21/6458 356/512 |
| 2006/0283945 | A1 | 12/2006 | Excoffier | |
| 2007/0216906 | A1 | 9/2007 | Javidi et al. | |
| 2008/0018966 | A1 * | 1/2008 | Dubois | G01B 9/021 359/9 |
| 2008/0032325 | A1 | 2/2008 | DiMarzio | |
| 2008/0113340 | A1 | 5/2008 | Schlegel | |
| 2008/0137933 | A1 | 6/2008 | Kim | |
| 2008/0242556 | A1 | 10/2008 | Cao et al. | |
| 2008/0317325 | A1 | 12/2008 | Ortyn et al. | |
| 2009/0082637 | A1 | 3/2009 | Galperin | |
| 2009/0092227 | A1 | 4/2009 | David | |
| 2009/0244667 | A1 | 10/2009 | Frentz | |
| 2009/0296083 | A1 | 12/2009 | Saski et al. | |
| 2009/0305393 | A1 | 12/2009 | Joeris | |
| 2010/0034442 | A1 | 2/2010 | Minakuchi | |
| 2010/0196871 | A1 | 8/2010 | Dodgson | |
| 2010/0315501 | A1 | 12/2010 | Ludwig | |
| 2011/0134426 | A1 * | 6/2011 | Kaduchak | G01N 15/1404 356/337 |
| 2011/0204256 | A1 | 8/2011 | Patt | |
| 2011/0212440 | A1 | 9/2011 | Viovy | |
| 2012/0015391 | A1 | 1/2012 | Zhang et al. | |
| 2012/0200901 | A1 * | 8/2012 | Dubois | G02B 21/00 359/15 |
| 2012/0218379 | A1 | 8/2012 | Ozcan | |
| 2014/0038171 | A1 | 2/2014 | Metzger et al. | |
| 2014/0049634 | A1 | 2/2014 | Tafas | |
| 2014/0193850 | A1 | 7/2014 | Jooris et al. | |
| 2014/0195568 | A1 | 7/2014 | Mathuis et al. | |
| 2014/0329231 | A1 | 11/2014 | Magniette | |
| 2014/0349336 | A1 | 11/2014 | Magniette | |
| 2014/0376816 | A1 * | 12/2014 | Lagae | G01N 15/1436 382/195 |
| 2015/0248109 | A1 | 9/2015 | Mathuis et al. | |
| 2017/0023472 | A1 | 1/2017 | Pavillion et al. | |
| 2017/0205222 | A1 | 7/2017 | Mathuis et al. | |
| 2017/0261930 | A1 | 9/2017 | Mathuis et al. | |

FOREIGN PATENT DOCUMENTS

| | | | |
|---|---|---|---|
| EP | 1524491 | A1 | 4/2005 |
| EP | 2008715 | A1 | 12/2008 |
| EP | 2602608 | | 6/2013 |
| WO | WO 98/57152 | | 12/1998 |
| WO | WO 99/44593 | A1 | 9/1999 |
| WO | WO 2004/057464 | A2 | 7/2004 |
| WO | WO 2004/102111 | A1 | 11/2004 |
| WO | WO 2006/047252 | A1 | 5/2006 |
| WO | WO 2007/073345 | A1 | 6/2007 |
| WO | WO 2009/051741 | A2 | 4/2009 |
| WO | WO 2009/151632 | | 12/2009 |
| WO | WO 2009/154558 | A1 | 12/2009 |
| WO | WO 2011/042442 | A1 | 4/2011 |
| WO | WO 2011/068764 | A2 | 6/2011 |
| WO | WO 2011/099925 | A1 | 8/2011 |
| WO | WO 2011/154143 | A1 | 12/2011 |
| WO | WO 2013/120886 | A1 | 8/2013 |
| WO | WO 2014/044823 | A1 | 3/2014 |

OTHER PUBLICATIONS

Fook Chiong Cheong et al. “Flow visualization and flow cytometry with holographic video microscopy”, Proceedings of the SPIE—The International Society for Optical Engineering SPIE—The International Society for Optical Engineering USA, vol. 7619, 2010, XP040518833, ISSN: 0277-786X. Published Feb. 10, 2010.

Yong-Seok Choi et al. “Lateral and cross-lateral focusing of spherical particles in a square microchannel”, Lab on a Chip, vol. 11, No. 3, pp. 460-465, XP55032064, ISSN: 1473-0197, DOI: 10.1039/cOlc00212g. Published Feb. 1, 2011.

Frank Dubois et al. “Applications of digital holographic microscopes with partially spatial coherence sources”, Journal of Physics: Conference Series, Institute of Physics Publishing, Bristol, GB, vol. 139, No. 1, p. 12027, XP020148183, ISSN: 1742-6596. Published Nov. 1, 2008.

Beitsch et al., “Detection of carcinoma cells in the blood of breast cancer patients,” The American Journal of Surgery, vol. 180, pp. 446-449 (Dec. 2000).

Boulet et al., “Cancer Epidemiology,” Biomarkers & Prevention, 2008, 17(4): 810-817.

Daneshpanah et al., “3D Holographic Imaging and Trapping for Non-Invasive Cell Identification and Tracking,” Journal of Display Technology, vol. 6(10), pp. 490-499 (Oct. 2010).

(56) References Cited

OTHER PUBLICATIONS

Extended European Search Report for European Patent Application No. 16151897.2, dated Jul. 21, 2016.0.
Fu et al., "Quantitative DIC microscopy using an off-axis self-interference approach," Optics Letters, vol. 35(14), pp. 2370-2372 (Jul. 15, 2010).
Indebetouw, G. et al. Feb. 20, 2007. Scanning holographic microscopy with resolution exceeding the Rayleigh limit of the objective by superposition of off-axis holograms. Applied Optics 46(6): 993-1000. speif. pp. 993, 994.
Kemper, B. et al. Feb. 1, 2008. Digital holographic microscopy for live cell applications and technical inspection. Applied Optics 47(4): A52-A61. specif. pp. A52, 53, 56, 59.
Kemper et al., "Monitoring of laser micro manipulated optically trapped cells by digital holographic microscopy," J Biophoton, vol. 3(7), pp. 425-431 (2010).
Kemper et al., "Investigation of living pancreas tumor cells by digital holographic microscopy," Journal of Biomedical Optics, vol. 11(3), pp. 034005-1-034005-8 (May/Jun. 2006).
Kemper et al., "Simplified approach for quantitative digital holographic phase contrast imaging of living cells," Journal of Biomedical Optics, vol. 16(2), pp. 026014-1-026014-4 (Feb. 2011).
Kemper et al., "Self interference digital holographic microscopy approach for inspection of technical and biological phase specimens," Proceedings of the SPIE—The International Society for Optical Engineering SPIE—The International Society for Optical Engineering USA, vol. 8082, May 23, 2011.
Lee et al., "Incremental feature weight learning and its application to a shape-based query system," Pattern Recognition Letters, vol. 23, pp. 865-874 (2002).
Marin et al., "A meta-index for querying distributed moving object database servers," Information Systems, vol. 35, pp. 637-661 (2010).
McClatchey et al., "Object Databases in a Distributed Scientific Workflow Application," Information Technology, 1997, BIWIT '97., Proceedings of the Third Basque International Workshop on Biarritz, France, Jul. 2-4, 1997; Los Alamitos, CA, USA, IEEE Comput. Soc. US, Jul. 2, 1997, pp. 11-21.
Moon et al., "Automated Three-Dimensional Identification and Tracking of Micro/Nanobiological Organisms by Computational Holographic Microscopy," Proceedings of the IEEE, vol. 97(6), pp. 990-1010 (Jun. 2009).
Nenadic et al., "A Possibility of Applying Differential Digital Holography in Manufacturing Process," 48th International Symposium ELMAR-2006, Jun. 7-9, 2006, Zadar, Croatia, pp. 103-106.
Owens et al., "Distinguishing Prostatic from Colorectal Adenocarcinoma on Biopsy Samples, The Role of Morphology and Immunohistochemistry," Arch Pathol Lab Med, vol. 131, pp. 599-603 (Apr. 2007).
Sahasranuddhe et al., Future Microbiol., 2011 6(9):1-25.
Sun et al., "Visualization of fast-moving cells in vivo using digital holographic video microscopy," Journal of Biomedical Optics, vol. 13(1), pp. 014007-1-014007-9 (Jan./Feb. 2008).
Reese et al., "Quantitative Analysis of Living Cells by Digital Holographic Microscopy," Biomedical Science & Engineering Conference, 2009, First Annual Ornl, IEEE, Piscataway, New Jersey, USA, pp. 1-4 (Mar. 18, 2009).
Weigum et al., "Nano-Bio-Chip Sensor Platform for Examination of Oral Exfoliative Cytology," Cancer Prevention Research, vol. 3, pp. 518-528 (2010).
White et al., "Isolation of Stool-Derived Mucus Provides a High Yield of Colonocytes Suitable for Early Detection of Colorectal Carcinoma," Cancer Epidemiol Biomarkers Prev, vol. 8, pp. 2006-2013 (2009).
Zhou et al., "An Image Clustering and Retrieval Framework Using Feedback-based Integrated Region Matching," 2009 International Conference on Machine Learning and Applications, 2009, ICMLA '09, IEEE, Piscataway, New Jersey, USA, Dec. 13, 2009, pp. 596-601.
International Search Report for Application No. PCT/EP2014/066312, dated Jan. 10, 2014, in 3 pages.
Kosmeier et al., "Determination of the Integral Refractive Index of Cells in Suspension by Digital Holographic Phase Contrast Microscopy", Biophotonics: Photonic Solutions for Better Health Care, Proc. of SPIE col. 6991, 699110, (2008).
Ling et al., "Application of Flow Cytometry for Biomarker-Based Cervical Cancer Cells Detection," Diagnotic Cytopathology, vol. 36, No. 2, dated 2008.
Mann et al., "Dual Modality Live Cell Imaging with Multiple-Wavelength Digital Holography and Epi-Fluorescence," Topical Editor: Dr. Tristan Colomb, 3D Res.2, Accepted: Nov. 3, 2010.
Pavillon, et al., "Cell Morphology and Intracellular ionic homeostasis explored with a multimodal approach combining epifluorescene and digital holographic microscopy," Journal of Biophotonics, vol. No. 7, pp. 432-436, Accepted Mar. 5, 2010.
Pin Wang et al., "Nanoscale Nuclear Architecture for Cancer Diagnosis beyond Pathology Via Spatial-Domain Low-Coherence Quantative Phase Microscopy," Journal of Biomedical Optics , vol. 15(6), 066028, dated Nov./Dec. 2010.
Wikipedia "Quantitative Phase-Contrast Microscopy" retreieved from http://en.wikipedia.org/w/index.php?title=Quantitative_phase-contrast_microscopy&oldid=734365574, last modified on Aug. 13, 2016.
Yeom, "Automatic Identification of Biological Microorganisms using Three-Dimensional Complex Morphology," Journal of Biomedical Optics, vol. 11(2), 0124017, dated Mar./Apr. 2006.
International Preliminary Report for Application No. PCT/EP2013/052852, dated May 11, 2014, in 13 pages.
International Search Report for Application No. PCT/EP2013/052852, dated Apr. 25, 2013, in 5 pages.

* cited by examiner

FLOW CYTOMETER WITH DIGITAL HOLOGRAPHIC MICROSCOPE

CROSS-REFERENCE TO RELATED APPLICATIONS

This application is the U.S. National Phase under 35 U.S.C. § 371 of International Application PCT/EP2013/052852, filed Feb. 13, 2013, which claims priority to EP 12155139.4, filed Feb. 13, 2012.

TECHNICAL FIELD

The invention pertains to the technical field of observing, measuring, analysing and/or separating objects, including biological organisms such as cells, bacteria, yeasts, micro-organisms, nematodes and non-biological objects, impurities, contaminants, or any combination thereof, in a liquid sample, using a digital holographic microscope (DHM). More in particular, a system is disclosed whereby the objects flow through the illumination beam of the DHM reactor in a flow-cytometric set-up, whereby objects may be observed, measured, analyzed, classified and possibly separated depending on their characteristics as observed by the DHM.

BACKGROUND

Flow cytometry is a technique for counting and examining microscopic particles, such as cells and chromosomes, by suspending them in a stream of fluid and passing them by an electronic detection apparatus. It allows simultaneous multiparametric analysis of the physical and/or chemical characteristics of up to thousands of particles per second. Flow cytometry is routinely used in the diagnosis of health disorders, especially blood cancers, but has many other applications in both research and clinical practice. A common variation is to physically sort particles based on their properties, so as to purify populations of interest.

Fluorescence-activated cell sorting is a specialized type of flow cytometry. It provides a method for sorting a heterogeneous mixture of biological cells into two or more containers, one cell at a time, based upon the specific light scattering and fluorescent characteristics of each cell. It is a useful scientific instrument, as it provides objective and quantitative recording of fluorescent signals from individual cells as well as physical separation of cells of particular interest. The cell suspension is entrained in the center of a narrow, rapidly flowing stream of liquid. The flow is arranged so that there is a large separation between cells relative to their diameter. A vibrating mechanism causes the stream of cells to break into individual droplets. The system is adjusted so that there is a low probability of more than one cell per droplet. Just before the stream breaks into droplets, the flow passes through a fluorescence measuring station where the fluorescent character of interest of each cell is measured. An electrical charging ring is placed just at the point where the stream breaks into droplets. A charge is placed on the ring based on the immediately prior fluorescence intensity measurement, and the opposite charge is trapped on the droplet as it breaks from the stream. The charged droplets then fall through an electrostatic deflection system that diverts droplets into containers based upon their charge. In some systems, the charge is applied directly to the stream, and the droplet breaking off retains charge of the same sign as the stream. The stream is then returned to neutral after the droplet breaks off.

Flow cytometry can thus be used to analyse objects and separate objects from others in a liquid sample. Hereby objects are suspended in a liquid and are lined up one-by-one, typically by using a low-density suspension of objects and drop-shaped nozzle out of which the object liquid is allowed to fall downwards in a narrow stream or in small droplets. The narrow stream passes in front of illumination means, typically a laser beam or a fluorescence activation light. The laser beam can scatter from the objects, or the illumination means can induce fluorescence in the objects if these have been marked with fluorescent markers. Based on the observed scattered and/or fluorescent response light, information about the individually scanned object can be obtained. This information can furthermore be used to separate this object from the beam. Hereto, a charge can be induced on the object or the liquid droplet in which the object is suspended, and the object can then be removed from the stream by applying an electrostatic field. Important in existing flow cytometry is that the microscopic particles such as objects are lined up one-by-one in a liquid flow when they pass through a measuring apparatus as the measuring apparatus is typically capable of obtaining information about the objects one at a time.

U.S. Pat. No. 7,463,366 discloses a method and device for obtaining a sample with three-dimensional microscopy, in particular a thick biological sample and the fluorescence field emitted by the sample. One embodiment includes obtaining interferometric signals of a specimen, obtaining fluorescence signals emanating from the specimen, recording these signals, and processing these signals so as to reconstruct three-dimensional images of the specimen and of the field of fluorescence emitted by the specimen at a given time. Another embodiment includes a digital holography microscope, a fluorescence excitation source illuminating a specimen, where the microscope and the fluorescence excitation source cooperate to obtain interferometric signals of the specimen and obtain fluorescence signals emanating from the specimen, means for recording the interferometric signals and fluorescence signals, and means for processing the interferometric signals and the fluorescence signals so as to reconstruct three-dimensional images of the specimen and of the field of fluorescence emitted by the specimen at a given time.

Patent application WO2004102111 discloses a compact microscope able to work in digital holography for obtaining high quality 3D images of samples, including fluorescent samples and relatively thick samples such as biological samples, said microscope comprising illumination means at least partially spatially coherent for illuminating a sample to be studied and a differential interferometer for generating interfering beams from said sample on the sensor of an electronic imaging device, said interferometer comprising namely tilting means for tilting by a defined angle one the interfering beams relatively to the other, said tilting resulting into a defined shift of said interfering beam on the sensor of the electronic imaging device, said shift being smaller than spatial coherence width of each beam, said microscope being able to be quasi totally preadjusted independently from the samples so that minimum additional adjustments are required for obtaining reliable 3D images of samples.

Hydrodynamic focusing is a technique used by e.g. microbiologists to provide more accurate results from flow cytometers or Coulter counters for e.g. determining the size of bacteria or cells. Cells are counted as they are forced to pass through a small tunnel, causing disruptions in a laser light beam or electricity flow. These disruptions are analyzed by the instruments. It is hard to create tunnels narrow enough for this purpose using ordinary manufacturing processes, as the diameter must be in the magnitude of micrometers, and the length of the tunnel should exceed several millimeters. Hydrodynamic focusing solves this problem by building up the walls of the tunnel from fluid, using the effects of fluid dynamics. A wide (hundreds of micrometers in diameter) tube made of glass or plastic is used, through which a “wall” of fluid called the sheath flow is pumped. The sample is injected into the middle of the sheath flow. If the two fluids differ enough in their velocity or density, they do not mix: they form a two-layer stable flow. The stability is required for a better quality of the measurement of the suspended objects.

WO 2011/068764 discloses a flow cytometer which includes a capillary having a sample channel, at least one vibration producing transducer coupled to the capillary, the at least one vibration producing transducer being configured to produce an acoustic signal inducing acoustic radiation pressure within the sample channel to acoustically concentrate particles flowing within a fluid sample stream in the sample channel; and an interrogation source having a violet laser and a blue laser, the violet and blue lasers being configured to interact with at least some of the acoustically concentrated particles to produce an output signal. A system as in WO 2011/068764 is an example of a flow cytometer with acoustic focusing, and more specifically a capillary-flow cytometer with acoustic focusing.

WO 1998/057152 discloses a method and apparatus for detecting a fluorescent substance tagged to a microparticle are described. The device comprises a single capillary flow carrier system for transporting the microparticle past a selected location, a source of electromagnetic radiation for irradiating the substance tagged to the microparticle, and a detection system for measuring fluorescent light emitted from the substance at the selected location. The method comprises transporting the microparticle to a selected location, irradiating a fluorescent substance tagged to the microparticle, and measuring the fluorescent light emitted from the fluorescent substance at the selected location. A system as in WO 1998/057152 or in WO 2011/068764 is an example of a capillary-flow cytometer.

Prior art flow cytometers have a number of disadvantages. One disadvantage is that the information which is obtained about the object from scattered light is limited. Since the resulting data from flow cytometric analysis is at an aggregate level, it is not easy to observe and measure individual object behavior. Another major disadvantage with a prior art flow cytometer is its low object throughput rate. Even for high-speed flow cytometers and sorters, this is still less than a few thousand objects per second. The throughput rate is related to the flow speed and is limited by the measuring apparatus, which needs to be able to provide a measurement of adequate quality on a moving particle. Typically, the quality of the measurement decreases when the flow speed increases and vice versa. A faster measuring technique, i.e. a technique doing measurements of adequate quality in a smaller period, thus allows for a higher throughput rates. Many experiments require a very large number of objects. This implies that even high-speed flow cytometers and sorters as available in the prior art need to run for long durations, which is not only an expensive proposition but may also pose quality issues because the objects sorted from such long runs may no longer be usable in scientific experiments. This problem may be further aggravated when the sorted objects need to be sterile.

Although high speed flow cytometers can give sterile objects, this makes the operation complex and further reduces the throughput. Most existing flow cytometric systems do not obtain an image of the objects, which may be desired, e.g. for later inspection or for updating an image database. In systems that do obtain an image of the objects, including biological organisms such as cells, bacteria, yeasts, micro-organisms, nematodes and non-biological objects, impurities, contaminants, or any combination thereof, the image is taken with a classical, e.g. a fluorescence or a projection, microscope, which necessitates lining up the objects in the focus of the microscope. Measurement results from objects which are lined up out of focus are usually rejected, which leads to a significant loss in efficiency and in information.

Further, flow cytometry has very sophisticated instrumentation, whereby only skilled and highly trained operators can run it and get any acceptable levels of performance from such an apparatus.

Also, flow cytometers are expensive instruments to purchase and maintain. A laser flow cytometer, which can only analyze but not sort, can be very expensive, especially for small laboratoria, while arc-lamp-based cytometers are only marginally cheaper. Flow cytometers with the additional sorting capability can cost almost double their cheaper versions. Additionally, operating a high-speed sort is another recurring expense that typically costs a substantial amount for each run.

The data acquired with the analysis or measuring apparatus of a prior art flow cytometer may not be accurate enough, it may not be obtained quickly enough, the apparatus may be too expensive, it may only give two-dimensional and/or analogue images. Prior art flow cytometers may use classical optical techniques to obtain an image of the object, whereby the object needs to be in the focus of the optical system. This has two main disadvantages: (i) one may not be able to obtain a good image from an object as it may not be straightforward to place the object in-focus, especially if it is a moving object as in a flow cytometer, and (ii) one can only obtain an image of one object at a time as only one object can be placed in-focus at a time. Furthermore, the gathered sample may need to be processed before analysis, which can be a time-consuming and labor-intensive procedure. Contamination may be an issue when the same apparatus is used to monitor or analyze different samples.

DHMs may provide images and/or directly digitalized information about samples which are superior to images and information obtained by other imaging or analysis techniques. Using a DHM as measurement apparatus of a flow cytometric system or in addition to a flow cytometer allows a user to obtain a three-dimensional picture of the objects suspended in the liquid. This picture is based on the recorded interferometric information recorded by the DHM. A DHM may obtain this information without the necessity of lining up the objects one-by-one in the focus of the microscope. In fact, the interferometric pattern recorded by the DHM allows post-acquisition focusing, resulting in the possibility of extracting a clear 3D image of an object from the digitalized interferometric pattern, preferably by post-acquisition software on an analysis computer, and this without the need for positioning the objects in the focus of a microscope or adapting the focus of the microscope to the position of the object. Moreover, the objects do not need to be lined up single file as a recorded interferometric pattern may comprise 3D information of a large number of objects. This leads to higher throughput rates when a DHM is used in or in conjunction with a flow cytometric system. Furthermore, the DHM may still be used in conjunction with fluorescent dyes or markers, the combination of which leads to an extensive set of observable parameters of a large number of suspended objects and quantities in a single run.

There remains a need in the art for a flow cytometer with improved measuring, observation, analysis and/or separation properties. Using a digital holographic microscope as a measurement apparatus of a flow cytometer will allow to obtain better information about the scanned objects than prior art flow cytometers, especially due to its post-acquisition focusing capabilities which eliminate the need for a focusing apparatus or focusing step in the imaging process. A DHM is furthermore well adapted to provide high-quality information about moving objects as it needs little time to make an interferometric or holographic image of an object. A holographic image contains substantially more information about an object than prior art measurements in flow cytometric systems, which are typically based on scattered and fluorescent light, can deliver.

There remains a need in the art for flow cytometers with an improved throughput rate. The quick acquisition times of a DHM allows a high throughput rate, higher than prior art flow cytometers, especially prior art cytometers which provide a similar amount and quality of information about the scanned objects. The DHM is also capable or gathering information of many objects in one recording step, especially due to its post-acquisition focusing capabilities. Hereby, it is not necessary to present the objects one-by-one in the focus of the microscope, but a hologram of many objects may be obtained.

There remains a need in the art for flow cytometers which are non-invasive to the objects which are scanned. This includes flow cytometers which need to introduce fluorescent or other markers into the objects, including biological organisms such as cells, bacteria, yeasts, micro-organisms, nematodes and non-biological objects, impurities, contaminants, or any combination thereof, which are to be scanned. Such marking can be expensive, time-consuming and invasive to the objects, whereby the object may not be used in further experiments anymore. Using a flow cytometer with a DHM solves this problem as a DHM provides a non-invasive and cost- and time-effective way of obtaining high-quality information about objects. No dyes or markers are needed for the same or an improved quality of the measurements. However, there is also a need in the art for flow cytometers which are capable of obtaining the combined information about suspended objects, as obtainable by a DHM and by fluorescence techniques, in a single run.

There further remains a need in the art for flow cytometers which are easily operated. A DHM can be made easy to operate and furthermore lends itself perfectly for automatisation as it offers digitalized information which can be stored electronically and/or easily transferred for further use.

There also remains a need in the art for flow cytometers which are cheaper to manufacture and to operate. Flow cytometers with a DHM have no need for dyes or markers, which results in lower operation costs. Furthermore, DHMs may comprise a partially coherent light source such as a LED, OLED, OLET or similar, instead of a highly-coherent light source such as a laser, hereby drastically reducing manufacturing costs.

The invention therefore aims to provide a flow cytometer comprising a digital holographic microscope for the observation of the objects in a liquid flow.

DHMs may provide images and/or directly digitalized information about samples which is superior to other imaging or analysis techniques. A DHM does not need a focusing system, as one can perform post-acquisition focusing techniques on the recorded interferometric pattern. Therefore, one can obtain a high-quality image of an object without the need of focusing, and one can obtain images of more than one object at a time, as these images can be acquired in a post-acquisition step. Furthermore, using prior art techniques, the gathered sample may need to be processed before analysis, which can be a time-consuming and labor-intensive procedure. Contamination may be an issue when the same apparatus is used to monitor or analyze different reactors, or the same reactor at different positions of times. Prior art techniques may not always provide the possibility of returning the sample to the reactor or to another reactor, or the possibility of real-time monitoring and providing timely feedback for adapting the reactor's environmental parameters.

SUMMARY OF THE INVENTION

The present invention provides but is not limited to a flow cytometric system for observing, analyzing and/or separating objects in a liquid sample, comprising a digital holographic microscope (DHM) and at least one fluidic system,

- whereby the DHM comprises illumination means, an interferometric system and digital recording means;
- whereby the fluidic system is capable of guiding said objects through an illumination beam of the illumination means of said DHM.
- whereby preferably the objects are any in the list of biological organisms, cells, cell pigments, DNA- and RNA-strands, chromosomes, proteins, micro-organisms, bacteria, viruses, yeasts, nematodes, enzymes, cytoplasm, membranes, protozoa, etc. and non-biological objects, impurities, contaminants, or any combination thereof;
- whereby preferably the fluidic system comprises a mechanism for inducing a liquid sample stream through the fluidic system, preferably said mechanism comprises a pump;
- whereby preferably the fluidic system comprises a stream size controlling device for controlling the transverse dimensions of a liquid sample stream inside said fluidic system, preferably said stream size controlling device is capable of lining up the objects one-by-one or multiple objects at a time in said liquid sample stream.

In a preferred embodiment the illumination means of the DHM comprise partially coherent light.

In a preferred embodiment the DHM is a differential DHM, a color or color-sensitive DHM, or a combination thereof.

In a preferred embodiment, said system comprises one or more fluorescent detectors for observing fluorescent light of the objects.

In a preferred embodiment the fluidic system comprises a capillary tube for capillary-flow cytometry.

In a preferred embodiment the fluidic system comprises a hydrodynamic focusing system for providing a narrow tunnel by sheath flow through which the liquid sample with objects can flow.

In a preferred embodiment the fluidic system comprises an acoustic focusing system for acoustically concentrating objects flowing in said liquid sample stream.

In a preferred embodiment the flow cytometric system comprises an object sorting system for separating objects according to properties which are measurable by said DHM.

In a preferred embodiment said objects are cells. In a more preferred embodiment said cells can be separated according a property which indicates that said cells are anomalous, e.g. infected by human papillomavirus (HPV).

In a preferred embodiment, the present invention provides a flow cytometric system as described above, comprising at least one pumping system connected to said one or more fluidic systems and capable of inducing a fluid flow in said fluidic systems.

In a preferred embodiment, the present invention provides a flow cytometric system as described above, whereby at least one fluidic system forms a circuit between a sample reservoir and said DHM and back to said reservoir and/or to one or more other reservoirs.

In a preferred embodiment, the present invention provides a flow cytometric system as described above, whereby at least one fluidic system comprises a reservoir attachment system for easily attaching and/or detaching said fluidic system to a reservoir, whereby leakage of fluid is prevented.

In a preferred embodiment, the present invention provides a flow cytometric system as described above, whereby at least one fluidic system comprises a fluid-tight flexible, movable and/or bendable part which, when compressed, pulled and/or pushed results in a fluid flow in said fluidic system.

In a preferred embodiment, the present invention provides a flow cytometric system as described above, comprising a pumping system with a pump connected to said fluidic system, capable of compressing, pulling and/or pushing said fluid-tight flexible, movable and/or bendable part, thereby inducing a fluid flow in said fluidic system.

In a preferred embodiment, the present invention provides a flow cytometric system as described above, whereby at least one pumping system comprises a, preferably continuous, pump such as a peristaltic pump, capable of inducing a, preferably continuous, fluid flow in a fluidic system to which said pump is connected.

In a further aspect, the present invention provides a tube for a fluidic system of a flow cytometric system as described above.

In a preferred embodiment, said tube is autoclavable.

In a preferred embodiment, the present invention provides a tube as described above, whereby said part comprises a capillary part for narrowing a liquid sample stream through said tube.

In a further aspect, the present invention provides a fluidic system for a flow cytometric system as described above, comprising one or more parts which are at least partially transparent for the illumination means of the DHM of said flow cytometric system, such as at least partially transparent tubes, reservoirs, sheath fluid, or transparent interruptions or openings, e.g. in tubing.

In a different aspect, the present invention provides a flow cytometric method for observing, analyzing and/or separating objects in a liquid sample, comprising the steps of:

- providing a DHM comprising illumination means, an interferometric system and digital recording means;
- providing a fluidic system preferably comprising a mechanism to induce a liquid sample stream of the liquid sample through the fluidic system;
- inducing a liquid sample stream through the fluidic system;
- guiding said objects, lined up one-by-one or multiple objects at a time, through an illumination beam of the illumination means of said DHM;
- observing and/or analyzing said objects with the aid of said DHM;
- preferably separating said objects from said liquid sample stream according to observed properties of said objects, whereby preferably said objects are biological organisms such as cells, bacteria, yeasts, micro-organisms, nematodes and non-biological objects, impurities, contaminants, or any combination thereof, whereby preferably said objects are lined up by capillarity, capillary flow, acoustic focusing and/or hydrodynamic focusing.

DETAILED DESCRIPTION OF THE INVENTION

Figure 1:
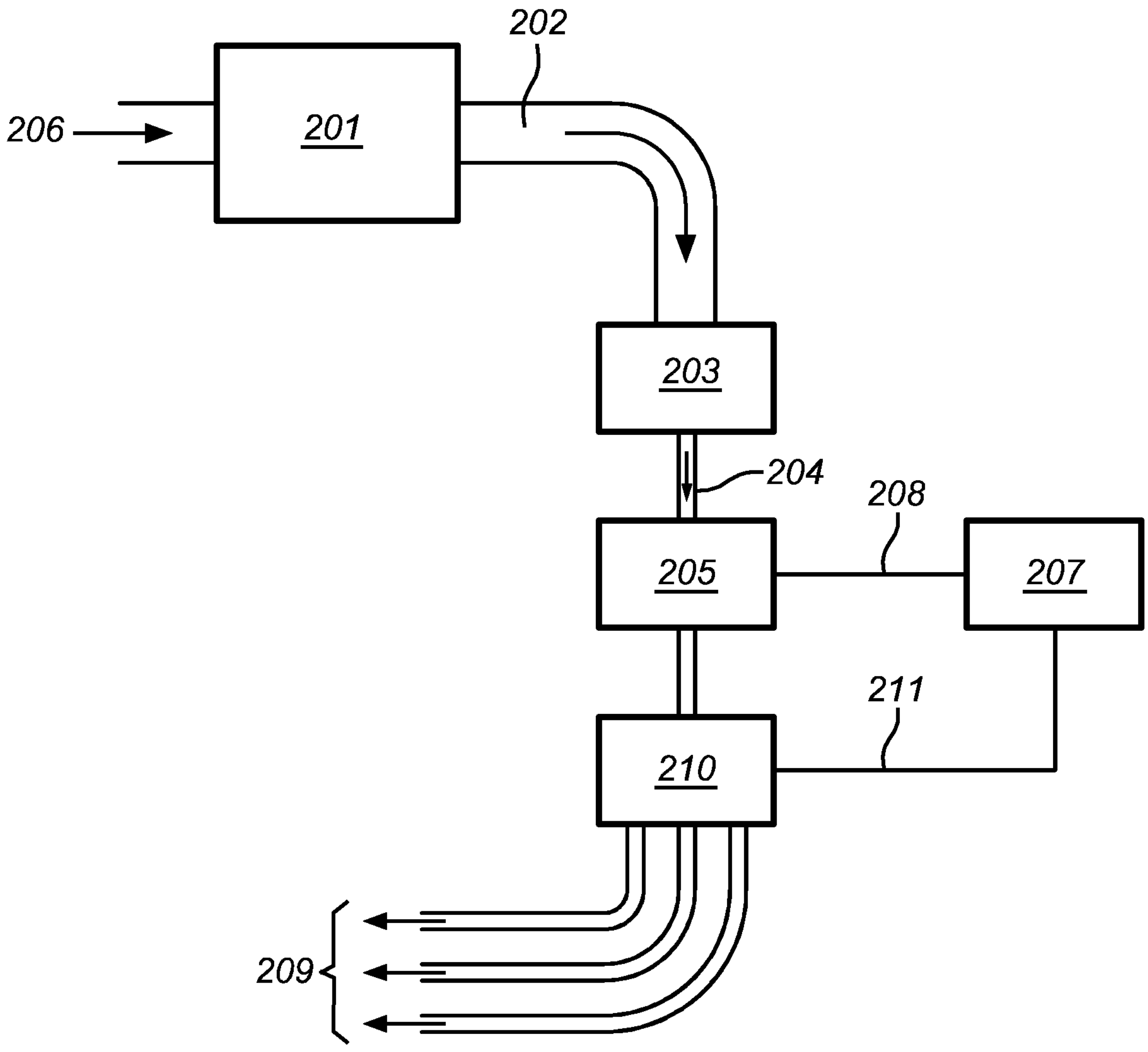
FIG. 1 is a flow chart illustrating a flow cytometric system according to the present invention.

The present invention concerns a flow cytometric system and method for observing, analyzing and/or separating objects in a liquid sample. The present invention also concerns a fluidic system of such a flow cytometric system and a tube for such a fluidic system.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight" (weight percent), here and throughout the description unless otherwise defined, refers to the relative weight of the respective component based on the overall weight of the formulation.

In a first aspect, the present invention provides a flow cytometric system for observing, analyzing and/or separating objects in a liquid sample, comprising a digital holographic microscope (DHM) and at least one fluidic system, whereby the DHM comprises illumination means, an interferometric system and digital recording means;

whereby the fluidic system is capable of guiding said objects through an illumination beam of the illumination means of said DHM.

whereby preferably the objects are any in the list of biological organisms, cells, cell pigments, DNA- and RNA-strands, chromosomes, proteins, micro-organisms, bacteria, viruses, yeasts, nematodes, enzymes, cytoplasm, membranes, protozoa, etc. and non-biological objects, impurities, contaminants, or any combination thereof;

whereby preferably the fluidic system comprises a mechanism for inducing a liquid sample stream through the fluidic system, preferably said mechanism comprises a pump;

whereby preferably the fluidic system comprises a stream size controlling device for controlling the transverse dimensions of a liquid sample stream inside said fluidic system, preferably said stream size controlling device is capable of lining up the objects one-by-one or multiple objects at a time in said liquid sample stream.

Using a DHM to measure and/or analyze objects such as biological organisms, cells, cell pigments, DNA- and RNA-strands, chromosomes, proteins, micro-organisms, bacteria, viruses, yeasts, nematodes, enzymes, cytoplasm, membranes, protozoa, etc. and non-biological objects, impurities, contaminants, or any combination thereof, has many advantages over other techniques, in particular other microscopic techniques, which is explained throughout this document. The advantages include the possibility of post-acquisition focusing which allows one to obtain information of multiple objects without an optical focusing step. Combining a DHM with a stream or flow of objects in a liquid whereby said objects are lined up single file or whereby more than one object at a time is presented when they are to be measured or observed by the DHM, allows to obtain a detailed analysis of individual objects in the sample, the analysis being of an improved quality as compared to prior art flow cytometric systems. Furthermore, this allows a fast, detailed and individualized scanning or analysis of a large number of objects by a DHM, faster than analyzing the same number of objects in a prior art DHM.

Using a DHM in a flow-cytometric system offers many advantages as compared to other analyzing/monitoring techniques, such as the possibility of inline 3D/4D monitoring instead of the work-intensive method of collecting or hand-collecting samples at specific moments and from specific reactors and subsequent analysis on (2D/3D) microscopic systems such as traditional microscopes, phase contrast microscopes or confocal microscopes;

the greater amount of information about a sample gathered in a shorter period of time compared to other microscopic techniques;

the possibility of automated digitalization and even automated qualification and quantification of the sample, etc.

DHM offers directly digitalized phase information which allows 3D imaging. This is faster than other 3D imaging techniques such as CT scans which first obtain a large set of 2D images from which a 3D image is reconstructed, possibly after an extra digitalization step. Therefore, the present invention leads to a faster, more accurate and more reliable analyzing and/or monitoring of reactors by using DHM as an observation, analysis and/or monitoring apparatus or mechanism. DHM is also more apt than other microscopy system for analyzing fluid, more preferably liquid, samples, especially for obtaining 3D information, because it is faster and more accurate than e.g. CT techniques.

Digital Holographic Microscopy is a technique which allows a recording of a 3D sample or object without the need of scanning the sample layer-by-layer. In this respect DHM is a superior technique to confocal microscopy. In DHM, a holographic representation is recorded by a digital camera such as a CCD- or a CMOS-camera, which can subsequently be stored or processed on a computer.

To make a holographic representation, or hologram, traditionally a highly coherent light source such as laser-light, is used to illuminate the sample. In the most basic set-up, the light form the source is split into two beams, an object beam and a reference beam. The object beam is sent via an optical system to the sample and interacts with it, thereby altering the phase and amplitude of the light depending on the object's optical properties and 3D shape. The object beam which has been reflected on or transmitted through the sample, is then made (e.g. by set of mirrors and/or beam splitters) to interfere with the reference beam, resulting in an interference pattern which is digitally recorded. Since the hologram is more accurate when object beam and reference beam have comparable amplitude, an absorptive element can be introduced in the reference beam which decreases its amplitude to the level of the object beam, but does not alter the phase of the reference beam or at most changes the phase globally, i.e. not dependent on where and how the reference beam passes through the absorptive element. The recorded interference pattern contains information on the phase and amplitude changes which depend on the object's optical properties and 3D shape.

An alternative way of making a hologram is by using the in-line holographic technique. In-line DHM is similar to the more traditional DHM, but does not split the beam, at least not by a beam splitter or other external optical element. In-line DHM is most preferably used to look at a not-too-dense solution of particles, e.g. cells, in a fluid. Thereby some part of the at least partially coherent light will pass through the sample without interacting with the particles (reference beam) and interfere with light that has interacted with the particles (object beam), giving rise to an interference pattern which is recorded digitally and processed. In-line DHM is used in transmission mode, it needs light with a relatively large coherence length, and cannot be used if the samples are too thick or dense.

Another DHM technique called differential DHM (DDHM) is disclosed in European patent EP 1 631 788.

DDHM is different to the other techniques in that it does not really make use of reference and object beams. In a preferred set-up of DDHM, the sample is illuminated by illumination means which consist of at least partially coherent light in reflection or in transmission mode. The reflected or transmitted sample beam can be sent through an objective lens and subsequently split in two by a beam splitter and sent along different paths in a differential interferometer, e.g. of the Michelson or Mach-Zehnder type. In one of the paths, a beam-bending element or tilting means is inserted, e.g. a transparent wedge. The two beams are then made to interfere with each other in the focal plane of a focusing lens and the interference pattern in this focal plane is recorded digitally and stored by e.g. a CCD-camera connected to a computer. Hereby, due to the beam-bending element, the two beams are slightly shifted in a controlled way and the interference pattern depends on the amount of shifting. Then the beam-bending element is turned, thereby altering the amount of shifting. The new interference pattern is also recorded. This can be done a number N of times, and from these N interference patterns, the gradient (or spatial derivative) of the phase in the focal plane of the focusing lens can be approximately computed. This is called the phase-stepping method, but other methods of obtaining the phase gradient are also known, such as a Fourier transform data processing technique. The gradient of the phase can be integrated to give the phase as a function of position. The amplitude of the light as a function of position can be computed from the possibly but not necessarily weighted average of the amplitudes of the N recorded interference patterns. Since phase and amplitude are thus known, the same information is obtained as in a direct holographic method (using a reference and an object beam), and a subsequent 3D reconstruction of the object can be performed. A differential DHM has certain advantages over other types of DHMs, one of them being the reduced manufacturing and operating cost. Furthermore, with a differential DHM, one does not need to introduce a sample in between the interferometric components, which leads to better quality of the obtained hologram and a stronger and more shock-resistant DHM. Therefore, in a preferred embodiment the DHM is a differential DHM.

The use of DHM in a diagnostic setting has many advantages which makes it the ideal technique to implement in a setting such as in the current invention. Besides a bright field image, a phase shift image is created as well. The phase shift image is unique for DHM and gives quantifiable information about optical distance. In reflection DHM, the phase shift image forms a topography image of the object.

Transparent objects, like living biological cells, are traditionally viewed in a phase contrast microscope or in a differential interference contrast microscope. These methods visualize phase shifting transparent objects by distorting the bright field image with phase shift information. Instead of distorting the bright field image, transmission DHM creates a separate phase shift image showing the optical thickness of the object. Digital holographic microscopy thus makes it possible to visualize and quantify transparent objects and is therefore also referred to as quantitative phase contrast microscopy. More so, DHM allows imaging subcellular structures in three dimensions.

An object image is calculated at a given focal distance. However, as the recorded hologram contains all the necessary object wave front information, it is possible to calculate the object at any focal plane by changing the focal distance parameter in the reconstruction algorithm. In fact, the hologram contains all the information needed to calculate a complete image stack. In a DHM system, where the object wave front is recorded from multiple angles, it is possible to fully characterize the optical characteristics of the object and create tomography images of the object.

Furthermore, as DHM systems do not have an image forming lens, traditional optical aberrations do not apply to DHM. Optical aberrations are "corrected" by design of the reconstruction algorithm. A reconstruction algorithm that truly models the optical setup will not suffer from optical aberrations. In optical microscopy systems, optical aberrations are traditionally corrected by combining lenses into a complex and costly image forming microscope objective. Furthermore, the narrow focal depth at high magnifications requires precision mechanics. Lastly, the needed components for a DHM system are inexpensive optics and semiconductor components, such as a laser diode and an image sensor. The low component cost in combination with the auto focusing capabilities of DHM, make it possible to manufacture DHM systems for a very low cost.

In a preferred embodiment the DHM is a differential DHM, a color or color-sensitive DHM, or a combination thereof. Typically, a differential DHM can used if cost of the flow cytometric system is to be kept low. A color or color-sensitive DHM, which comprises more than one, e.g. three, illumination means at or around different wavelengths, allows one to obtain more detailed and/or colored images of the objects.

In a preferred embodiment, said system comprises one or more fluorescent detectors for observing fluorescent light of the objects or impedance detectors for measuring the impedance of the objects. The flow cytometric system of the present invention may comprise measurement components which are used in prior art flow cytometric systems, such as measurement systems of impedance (or conductivity) and optical systems—lamps (mercury, xenon); high-power water-cooled lasers (argon, krypton, dye laser); low-power air-cooled lasers (argon (488 nm), red-HeNe (633 nm), green-HeNe, HeCd (UV)); diode lasers (blue, green, red, violet) resulting in light signals. The DHM may thus be coupled to existing flow-cytometric systems, hereby increasing the information obtained in one run as compared to existing systems without a DHM.

In a preferred embodiment the fluidic system comprises a capillary tube for capillary-flow cytometry. In this way, the objects in the liquid sample, e.g. the cells, can be lined up single file or with multiple objects at a time in the capillary tube, e.g. without the need of a sheath fluid or other mechanism. By choosing the width of the capillary tube, it is also possible to control the number of objects which are exposed simultaneously to the illumination means of the DHM.

In a preferred embodiment the fluidic system comprises a hydrodynamic focusing system for providing a narrow tunnel by sheath flow through which the liquid sample with objects can flow. Hydrodynamic focusing is a very effective approach to position particles for analysis.

In a preferred embodiment the fluidic system comprises an acoustic focusing system for acoustically concentrating objects flowing in said liquid sample stream. A flow cytometer with an acoustic focusing system utilizes acoustic excitation, generated along the entire structure of e.g. a capillary tube, to both focus and concentrate sample particles to the interrogation region. Because acoustic methods both focus and concentrate particles, it is possible to maintain both conventional particle analysis rates as well as long transit times while using a fraction of the power and consumables of a flow cytometer without acoustic focusing system. The longer integration time allows conventional particle analysis using data acquisition systems that are less expensive, smaller and require less power, while still performing high sensitivity measurements. However, the benefits of acoustic focusing flow cytometry are not restricted to only the possible elimination of sheath fluid. Acoustic concentration also enables the analysis of extremely dilute samples on the order of several cells or particles per liter, as might be seen in a water monitoring application, at reasonable analysis rates. Since there is no sheath, it is also possible to repeatedly reanalyze particles of interest for reliable rare event analysis.

In a preferred embodiment the flow cytometric system comprises an object sorting system for separating objects according to properties which are measurable by said DHM. In a more preferred embodiment, said sorting system comprises a vibrating mechanism which causes the stream of objects to break into individual droplets. The system is adjusted so that there is a low probability of more than one object per droplet. Just before the stream breaks into droplets, the flow passes through illumination means of a DHM where pre-determined object properties can be measured or observed. An electrical charging ring is placed just at the point where the stream breaks into droplets. A charge is placed on the ring based on the immediately prior DHM measurement, and the opposite charge is trapped on the droplet as it breaks from the stream. The charged droplets then fall through an electrostatic deflection system that diverts droplets into containers based upon their charge. In another embodiment, the charge is applied directly to the stream, and the droplet breaking off retains charge of the same sign as the stream. The stream is then returned to neutral after the droplet breaks off.

In a preferred embodiment at least some of said objects are cells. Cells are objects which can be studied in much detail with DHM.

In a preferred embodiment at least some of said objects are impurities or contaminants, preferably comprising a size larger than a detection limit of the DHM. The detection limit of a DHM is typically of the order of the wavelength of the illumination beam, but may be decreased further to about half this wavelength, e.g. by using dark-field microscopic techniques.

In a preferred embodiment, said flow cytometric system comprises a fluorescence measuring system for measuring fluorescence response of the objects to the illumination means of said DHM. As such, the flow cytometric system may obtained combined information from the DHM and from a fluorescence analysis. For a fluorescence analysis, it may be necessary to treat the sample or the objects in the sample with at least one marker and/or dye. From the combined data from the DHM and the fluorescence measuring system, one may also look for correlations between e.g. cell characteristics which are obtained by the DHM and fluorescence signals of markers indicating the presence of viruses, proteins, DNA- or RNA-sequences, etc.

The fluorescent response of the objects in the sample may be spontaneous, or it may induced by the illumination means of the DHM and/or, in a preferred embodiment, the flow cytometric system comprises fluorescence illumination means for inducing a fluorescence response of said objects. These illumination means may comprise a light source with a spectrum, intensity and/or other properties which are capable for inducing fluorescence of the objects, which may be treated with markers and/or dyes.

In a more preferred embodiment said cells can be separated according one or more properties, preferably properties which indicates that said cells are anomalous, e.g. infected by human papillomavirus (HPV). These properties may include properties which are measurable by said DHM, such as cell size, cell height, cell optical height, cell type, nuclear size, nuclear height, nuclear optical height, lensing effect, etc. or any combination thereof. These properties may also be measurable by fluorescence response of the objects to illumination means, whereby the objects are preferably treated with at least one marker and/or dye, e.g. for marking the presence of anomalies, such as HPV. The property of lensing effect refers to the focusing or defocussing properties of the cells, which depend on the curvature of the object and the refraction index of the cell components and cell fluids, e.g. cytoplasma. Such a property can be used to determine whether the cell is alive or dead.

In a further aspect, the present invention provides a flow cytometric method for observing, analyzing and/or separating objects in a liquid sample, comprising the steps of:

- providing a DHM comprising illumination means, an interferometric system and digital recording means;
- providing a fluidic system preferably comprising a mechanism to induce a liquid sample stream of the liquid sample through the fluidic system;
- inducing a liquid sample stream through the fluidic system;
- guiding said objects, lined up one-by-one or multiple objects at a time, through an illumination beam of the illumination means of said DHM;
- observing and/or analyzing said objects with the aid of said DHM;
- preferably separating said objects from said liquid sample stream according to observed properties of said objects, whereby preferably said objects are biological organisms such as cells, bacteria, yeasts, micro-organisms, nematodes and non-biological objects, impurities, contaminants, or any combination thereof, whereby preferably said objects are lined up by capillarity, capillary flow, acoustic focusing and/or hydrodynamic focusing.

Other microscopic techniques than digital holographic microscopy in a flow cytometric system as described in this text, may not be fast or accurate enough for the monitoring of the processes in the reactor and circuit system. Such other microscopic techniques may not be applied inline, but need to take a sample, possibly apply a die or coloring, apply the sample to a slide, and use a microscope to observe the sample on the slide. This process is time consuming and labor intensive, and therefore not suitable for automation. Other microscope techniques may give analogue images, which then may be stored digitally e.g. through an additional scanning step. With DHM, the information is digitally obtained and can be processed digitally directly, i.e. one does not need an extra digitalization procedure. Furthermore, a DHM does not lead to the loss of the sample, as the sample can be returned to the reactor if desired. Other microscopic techniques may not have that advantage, due to the use of e.g. coloring, slides, adding necessary markers, etc. Nevertheless, fluorescence markers and dyes or other prior art techniques may still be used in conjunction with a DHM hereby increasing the amount of information which can be obtained from the suspended objects in a single run.

Generally, a DHM comprises illumination means which comprises a coherent light source or an at least partially coherent light source such as a LASER or LED, an interferometer which may comprise a set of mirrors and/or beam splitters, and digital recording means such as a CCD or CMOS camera and e.g. a flash card or magnetic recording device connected to it for long-time storage. A DHM may also comprise further optical components such as lenses, mirrors, prisms, attenuators, etc. Possibly, a DHM may comprise or may be connected to processing means such as a mainframe, a PC, a logical device such as a PLC, etc. A DHM may work in transmission and/or reflection mode, preferably depending on the nature of the sample which is to be observed. A DHM as used in the system of the present invention may be a traditional DHM, an in-line DHM, a differential DHM, a color or color-sensitive DHM, or another kind of DHM. Therefore, in a preferred embodiment, the illumination means of the DHM of said flow cytometric comprise partially coherent light. A partially coherent light source is in general cheaper than a coherent light source.

In an embodiment of said flow cytometric system, at least one fluidic system comprises one or more tubes which may come in direct contact with fluid from said reactor. Preferably said tubes comprise a bendable material which is still resistant against possible kinks. The advantage of using tubes in the fluidic system for guiding the fluid is that they can be produced cheaply and can be made long enough for the application at hand, or can be combined to a long fluid-guiding channel. In a more preferred embodiment, only the tubes, more preferably easily replaceable tubes, may come in direct contact with the fluid of the reactor. Thereby, other components of the fluidic system can be reused without the necessity of, possibly expensive, cleaning or decontamination procedures.

In a preferred embodiment, said at least one fluidic system comprises a part which is at least partially transparent for the illumination means of said DHM for obtaining phase information of said fluid sample.

For inline monitoring and/or analyzing the contents of a liquid sample reservoir with a flow-cytometric system according to the present invention, optical contact is needed between the DHM and at least a sample of the reservoir's contents, preferably without the need to definitively remove that sample from the reservoir. Therefore, said fluidic system may comprise at least a part which provides optical contact with the DHM, preferably the properties of said part are optimized to the specifications of the DHM. Furthermore, in a preferred embodiment, the fluidic system comprises one or more tubes for guiding a sample from the reservoir to the DHM and back to the reservoir and/or to one or more other reservoirs. In such an embodiment, the fluidic system can lead fluid from one reservoir to the DHM and then either back to the same reservoir, or to another, possibly depending on the information obtained by the DHM. Since the DHM is able to acquire information about a liquid sample fast and accurately, it can use this information in real-time to decide what needs to be done with the content of the observed sample. Thereto, in a preferred embodiment, the fluidic system may comprise one or more, preferably electronically steered, valves and a decision-making unit which is operably connected to the valves and the DHM and which decides on which valves to open and/or close at which time, depending on the information acquired by the DHM.

To avoid contamination of the sample taken from one reservoir e.g. by remains from another reservoir, the parts of the fluidic system circuits which may come into direct contact with fluids from reservoirs, should be easily replaceable. In this way, the parts that do not come into contact with fluid from reservoirs, can be re-used. This has many advantages: the replaceable parts may at least partly be made from cheap materials, only the part which should provide optimal optical contact with the DHM or stream size controlling device, e.g. a nozzle for narrowing a falling stream of liquid down to micrometer-size, may need to be expensive, the re-usable parts may be more expensive and of better quality as they will need to last a longer time. If the re-usable parts are cheap to manufacture, this is also fine. More in particular, the manufacturer of the system of the present invention has a choice in how to make the re-usable parts which can be optimized according to the specific use of the system. Replaceable parts of the system do not need to be decontaminated or sterilized or can be sterilized, e.g. autoclaved, before being connected to the fluidic system, hereby gaining time and saving costs, especially if many different types of samples need to analyzed by the same flow-cytometric system. Such replaceable parts may be produced in large quantities, leading to reduced costs. Therefore, in a preferred embodiment, the fluidic system comprises tubes which are easily replaceable and/or cheap to manufacture.

In a preferred embodiment, the system of the present invention comprises a central unit connected to the DHM or part of the DHM, which is capable of adjusting the DHM, in particular the working parameters of the DHM.

A fluid flow may be present due to natural phenomenon such as convection, conduction or radiation, by density or pressure differences induced by e.g. the reactions taking place in the reactor or heat gradients, by gravity, e.g. as induced by height differences, etc. If a fluid flow is desired, but is not occurring spontaneously or if the flow needs to be controlled, one or more pumping systems may be connected to the fluidic system in order to induce a flow in said system. Therefore, in a preferred embodiment, the flow cytometric system of the present invention comprises at least one pumping system connected to the fluidic system and capable of inducing a fluid flow in said fluidic system.

In a preferred embodiment, the flow cytometric system according to the present invention comprises at least one fluidic system which comprises a reservoir attachment system for easily attaching and/or detaching said fluidic system to a reservoir, whereby leakage of fluid is prevented. In a more preferred embodiment, said reservoir attachment system comprises a screw thread mounted on an outer surface which can be screwed into and out of a corresponding screw thread in an opening of a side or lid of said reservoir, hereby sealing said opening, i.e. preventing fluid from escaping the volume created by said reservoir and said fluidic system, whereby said reservoir attachment system comprises at least two passageways for fluid in-flux and fluid out-flux, hereby allowing transport of fluid from said reservoir to said DHM and possibly back via said fluidic system. The reservoir attachment system can be such that the fluidic system can be connected to a reservoir from the top, the side, the bottom or a combination thereof.

In a preferred embodiment, at least one fluidic system comprises a fluid-tight flexible, movable and/or bendable part which, when compressed, pulled and/or pushed results in a fluid flow in said fluidic system. As such, a fluid flow can be induced in the fluidic system without a high risk of leaks and without contamination of the actuator of the flow. In a more preferred embodiment, the fluid microscope system of the present invention comprises a pumping system connected to said fluidic system, capable of compressing, pulling and/or pushing said fluid-tight flexible, movable and/or bendable part, thereby inducing a fluid flow in said fluidic system.

In yet another aspect, the present invention provides an assembly of a flow cytometric system as disclosed in this document, connected to one or more reservoirs via a fluidic system. This reservoir may comprise a sample of objects suspended in a liquid, whereby the objects can be observed, measured, analyzed, classified and/or sorted by said flow cytometric system.

The invention is further described by the following non-limiting examples which further illustrate the invention, and are not intended to, nor should they be interpreted to, limit the scope of the invention.

EXAMPLES

FIG. 1 is a flow chart illustrating a flow cytometric system according to the present invention. A liquid sample, i.e. a sample of objects in suspension, from a reservoir (206) is introduced into a fluidic system. A stream is induced into the liquid sample by a pumping system (201), and the liquid sample is guided via a tube (202) of the fluidic system to a stream size controlling device (203) of the fluidic system. The stream of the liquid sample can be narrowed down (204) by the device (203) and sent to the DHM (205) of the flow cytometric system. This can be done by any technique, such as the ones described in this document: hydrodynamic focusing, acoustic focusing, capillarity, etc. and the liquid sample may simply fall through the illumination beam of the illumination means of the DHM or it may be guided through the illumination beam in a transparent tube, such as a transparent capillary tube, etc. The diameter or cross section of the narrowed stream (204) may be pre-set or it may be adjusted according to the specific liquid sample which is being analyzed or the specifications of the operator of the flow cytometric system. For a high throughput, the diameter can be chosen large such that many objects at a time are presented to the illumination beam and observed by the DHM. If the objects are to be sorted according to their measured properties, a small diameter leading to the lining up of the objects one-by-one, may be preferred. The information about the objects in the liquid sample stream is recorded by the DHM (205) and preferably send via a link (208) to a controlling, computing and database system (207). This system (207) may interpret the information as obtained by the DHM and may e.g. perform post-acquisition focusing for zooming in onto the individual objects and acquire information about these objects using imaging or image-interpreting software. The controlling system (207) may further be capable of storing or selectively storing the obtained information on the objects, and it may further steer a sorting apparatus (210) via a link (211) in order to sort the objects in the stream depending on a set of pre-determined criteria. The sorted objects can then be led to one or more reservoirs (209).

In the case of sorting, the flow cytometric system may also comprise a vibrating mechanism which causes the liquid sample stream to break into individual droplets. The system can then be adjusted so that there is a low probability of more than one object per droplet. An electrical charging ring is placed just at the point where the stream breaks into droplets. Just before the stream breaks into droplets, the flow passes through a DHM (205) where the properties of interest of each object is measured. An electrical charging ring is placed just at the point where the stream breaks into droplets. A charge is placed on the ring based on the immediately prior measured properties, and the opposite charge is trapped on the droplet as it breaks from the stream. The charged droplets then fall through an electrostatic deflection system that diverts droplets into containers based upon their charge. In some systems, the charge is applied directly to the stream, and the droplet breaking off retains charge of the same sign as the stream. The stream is then returned to neutral after the droplet breaks off.

FIGS. 2 to 6 show other embodiments of a flow cytometric system according to the present invention, whereby prior art flow cytometers are combined with a DHM.

Figure 2:
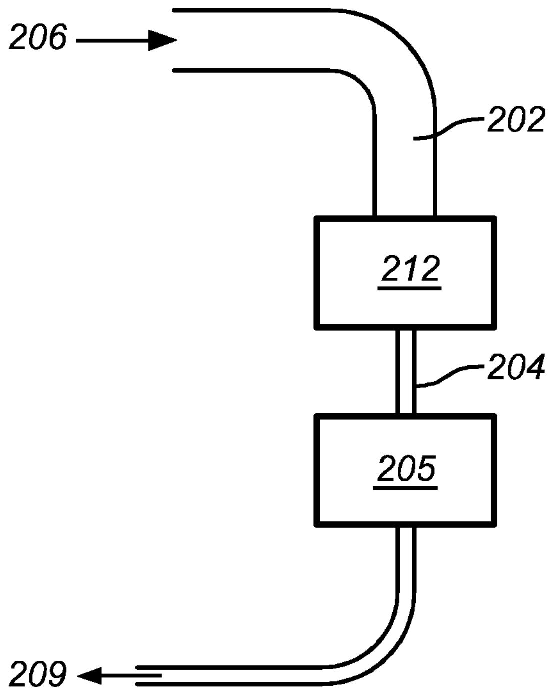
FIG. 2 shows how a liquid sample from a reservoir flows (202) to a flow cytometer as known in the prior art (212) and subsequently to a DHM.

In FIG. 2 a liquid sample from a reservoir (206) flows (202) to a flow cytometer as known in the prior art (212), e.g. a flow cytometer based on fluorescence or scattered laser light. The prior art flow cytometer (212) in FIG. 2 comprises a stream size controlling device which lines up the objects in the sample one-by-one, and the liquid sample stream coming out from the prior art flow cytometer (212) may be a narrowed sample stream (204) in which the objects are lined up one-by-one, said stream being guided or falling through the illumination beam of a DHM (205). Alternatively, the stream may be widened before presented to the illumination beam of the DHM (205). The DHM may obtain additional information about the objects, including e.g. 2D, 3D or 4D images. Afterwards, the liquid sample stream may be returned to a reservoir.

Figure 3:
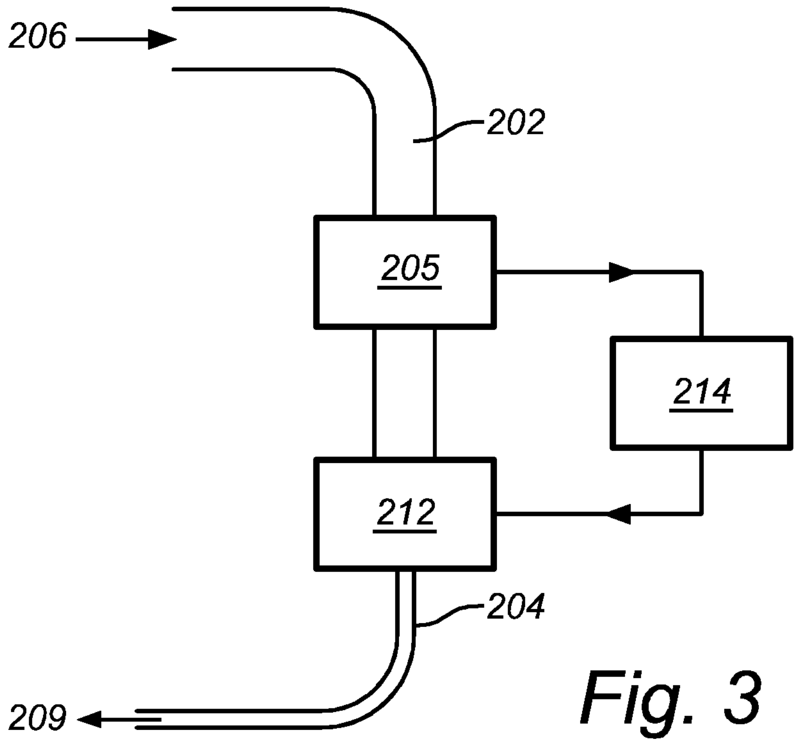
FIG. 3 shows an embodiment of a flow cytometric system according to the present invention, whereby a liquid sample stream is led to a DHM and subsequently to a prior art flow cytometer.

FIG. 3 shows an embodiment of a flow cytometric system according to the present invention, whereby a liquid sample stream is led to a DHM and subsequently to a prior art flow cytometer. The liquid sample is taken from a reservoir (206) and via the fluidic system (202) is led to a DHM (205) where multiple objects at a time are observed by the DHM (205). The liquid sample stream is then led by the fluidic system to a prior art flow cytometer (212) where it is narrowed down to line up the objects in the stream one-by-one. The narrow stream (204) is collected and guided to a reservoir (209) by the fluidic system. In such a setup, one may for instance use the information acquired by the DHM (205) to adapt the settings of the prior art flow cytometer (212) in real time e.g. via an automated control system (214).

Figure 4:
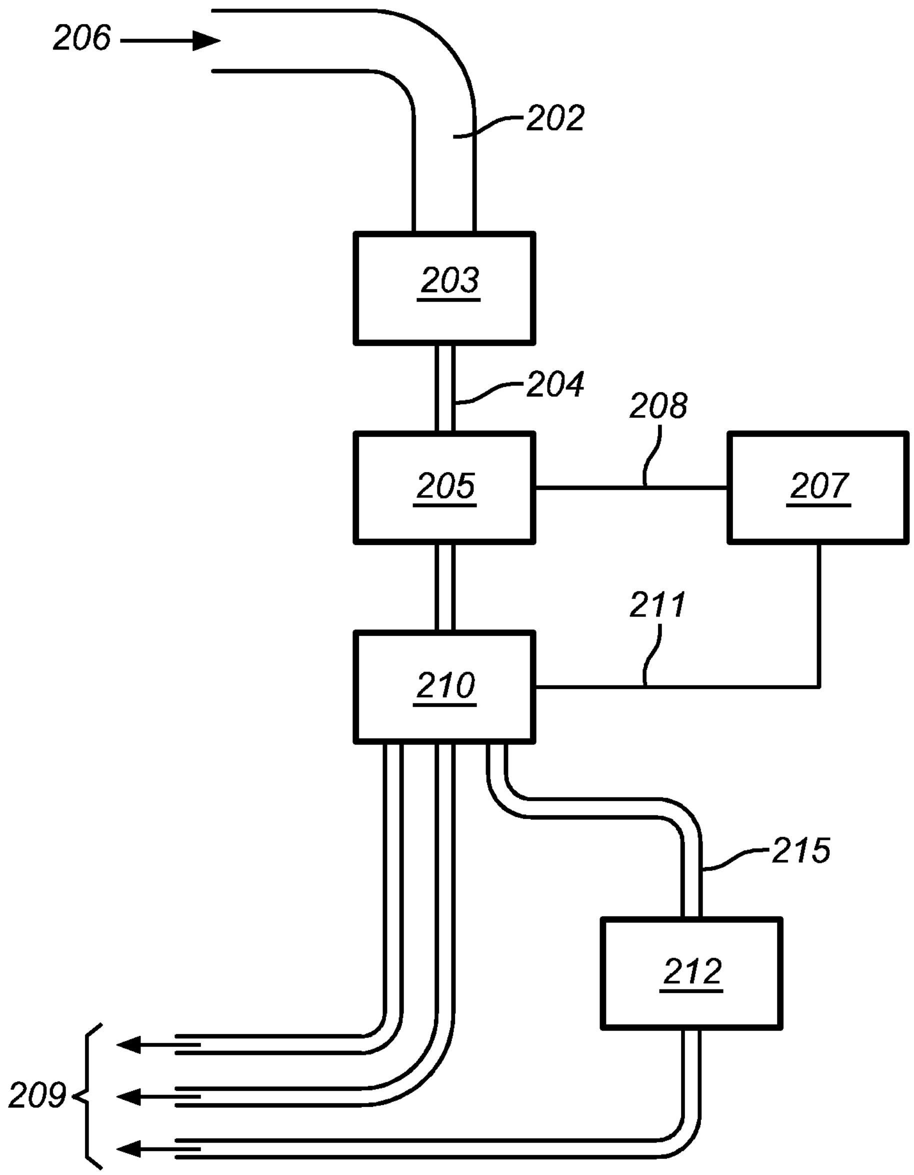
FIG. 4 shows an embodiment of a flow cytometric system according to the present invention, whereby the objects in a liquid sample stream are sorted according to the information acquired by a DHM and subsequently a subset of the objects is led to a prior art flow cytometer for obtaining additional information.

FIG. 4 shows an embodiment of a flow cytometric system according to the present invention, whereby the objects in a liquid sample stream are sorted according to the information acquired by a DHM and subsequently a subset of the objects is led to a prior art flow cytometer for obtaining additional information. The system illustrated in FIG. 4 is similar to the one illustrated in FIG. 1, with the addition of a prior art flow cytometer (212) along the flow of one of the sorted liquid sample streams (215). In this set-up, the prior art flow cytometer (212) may work independently from the controlling system (207) as the sorted liquid sample stream (215) already only contains those objects of interest. Alternatively, the flow cytometer (212) may be connected to the same controlling system (207) which can then serve as a centralized controlling, computing and/or data system.

Figure 5:
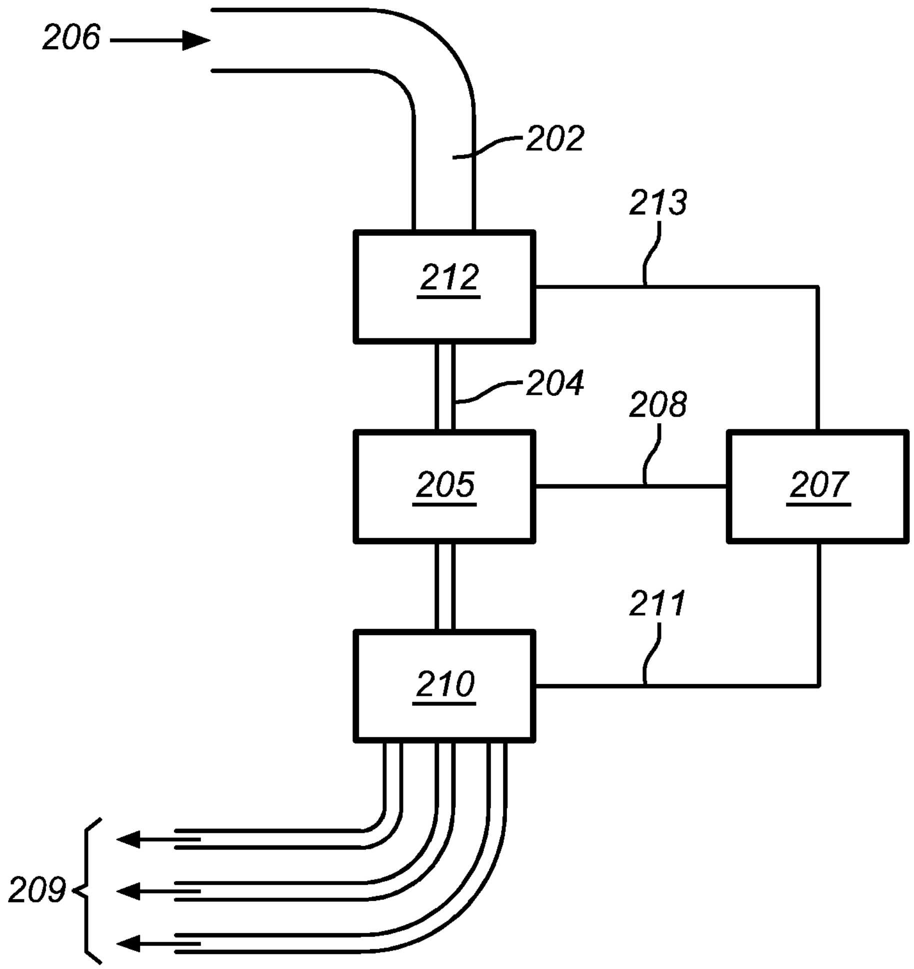
FIG. 5 shows an embodiment of a flow cytometric system according to the present invention, whereby the objects in a liquid sample stream are sorted according to the combined information acquired by a prior art flow cytometer and a DHM.

FIG. 5 shows an embodiment of a flow cytometric system according to the present invention, whereby the objects in a liquid sample stream are sorted according to the combined information acquired by a prior art flow cytometer and a DHM. The system illustrated in FIG. 5 is similar to the one illustrated in FIG. 1, with the addition of a prior art flow cytometer (212) with a stream size controlling device in the liquid sample stream (202). The prior art cytometer (212) provides information, e.g. fluorescence intensities or the dimensions of the objects as obtained by the observed scattering of laser light, to a control system (207) via link (213). The stream coming out of the prior art flow cytometer (212) may be kept narrow (204), i.e. the objects may still be lined up one-by-one. The objects are then led through the illumination beam of the illumination means of the DHM and information about the objects are obtained and sent through to the control system (207) via a link (208). The control system (207) may then combine in real time the information from the prior art flow cytometer and the DHM in order to steer the sorting apparatus (210), where the objects may be sorted according to their measured properties. The sorted liquid sample stream can be returned to one or more reservoirs (209).

Figure 6:
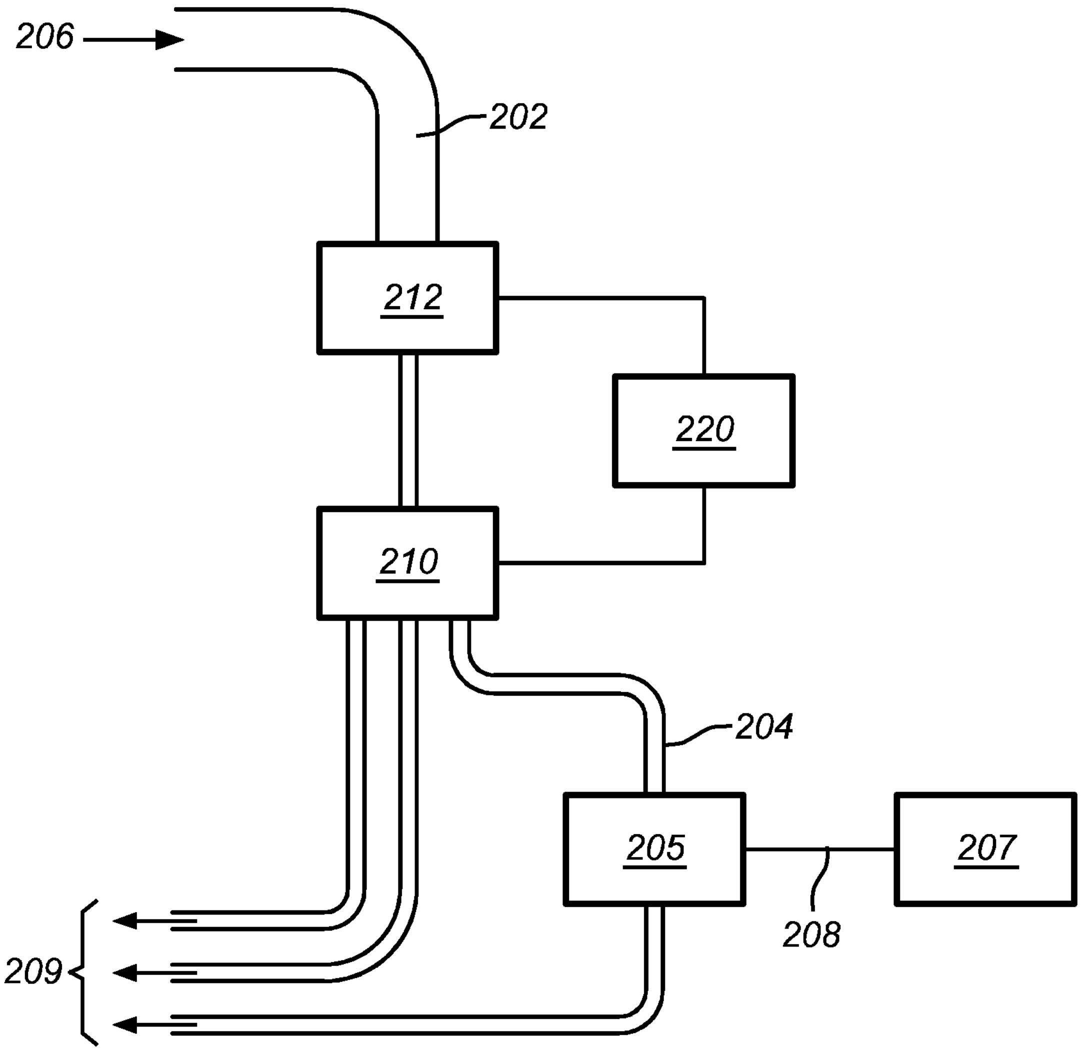
FIG. 6 shows an embodiment of a flow cytometric system according to the present invention, whereby the objects in a liquid sample stream are sorted according to the information acquired by a prior art flow cytometer and subsequently a sorted subset of the objects is led to a DHM for obtaining additional information.

FIG. 6 shows an embodiment of a flow cytometric system according to the present invention, whereby the objects in a liquid sample stream are sorted according to the information acquired by a prior art flow cytometer and subsequently a sorted subset of the objects is led to a DHM for obtaining additional information. Suspended objects in a liquid sample stream are taken from a reservoir (206) and via the fluidic system (202) are led to a prior art flow cytometer (212) which lines up the objects one-by-one. The information obtained by the prior art flow cytometer (212) is used to control, e.g. via a prior art control system (220), to sort the objects (210). One of the sorted liquid sample streams, which can still be kept narrow (204), i.e. the objects may be kept lined up one-by-one, is guided through the illumination beam of the DHM and the DHM obtains additional information about the sorted objects. The information can be analyzed and/or stored on a control system (207) via a link (208). The sorted liquid sample streams may be guided to one or more reservoirs (209.

It is supposed that the present invention is not restricted to any form of realization described previously and that some modifications can be added to the presented example of fabrication without reappraisal of the appended claims.

What is claimed is:

1. A flow cytometry system for observing, analyzing and/or separating objects in a liquid sample, comprising a digital holographic microscope (DHM) and at least one fluidic system, whereby the DHM comprises a coherent or partially coherent light source, an interferometric system and digital image sensor and recorder for storage of acquired images, whereby the fluidic system is capable of guiding said objects through an illumination beam of the light source of said DHM, whereby the fluidic system induces a liquid sample stream through the fluidic system, whereby the fluidic system controls transverse dimensions of the liquid sample stream inside said fluidic system by acoustic focusing and/or hydrodynamic focusing and is configured to line up multiple objects at a time in three dimensions in said liquid sample stream, whereby said DHM is capable of obtaining three-dimensional images of more than one object of the multiple objects at a time, whereby the light source of the DHM comprises a light-emitting diode (LED), an organic light-emitting diode (OLED) or an organic light-emitting field-effect transistor (OLET), and whereby the flow cytometry system further comprises a computer processor configured to perform post-acquisition focusing on the objects in said liquid sample stream by computer processing of the stored acquired three-dimensional images.

2. The flow cytometry system according to claim 1, wherein the objects comprise one or more of biological organisms, cells, cell pigments, DNA- and RNA-strands, chromosomes, proteins, micro-organisms, bacteria, viruses, yeasts, nematodes, enzymes, cytoplasm, membranes, protozoa, or non-biological objects.

3. The flow cytometry system according to claim 1, wherein the fluidic system comprises a pump to induce the liquid sample stream.

4. The flow cytometry system according to claim 1, wherein the fluidic system is capable of controlling a diameter or cross section of the liquid sample stream according to pre-set or adjustable levels.

5. The flow cytometry system according to claim 1, whereby the DHM is a differential DHM or a color DHM.

6. The flow cytometry system according to claim 1, whereby the fluidic system is capable of providing, by hydrodynamic focusing, a narrow tunnel by sheath flow through which the liquid sample with objects can flow.

7. The flow cytometry system according to claim 1, whereby the fluidic system is capable of acoustically concentrating objects flowing in said liquid sample stream.

8. The flow cytometry system according to claim 1, comprising a fluorescence detector for measuring fluorescence response of the objects to the coherent or partially coherent light source of said DHM.

9. The flow cytometry system according to claim 8, comprising a fluorescence light source different from the coherent or partially coherent light source for inducing a fluorescence response of said objects.

10. The flow cytometry system according to claim 1, wherein the system is capable of separating the multiple objects according to properties which are measurable by said flow cytometry system.

11. The flow cytometry system of claim 1, wherein the objects comprise impurities or contaminants with respect to the liquid sample being observed, analyzed, and/or separated.

12. A flow cytometry method for observing, analyzing and/or separating objects in a liquid sample, comprising the steps of:

providing a DHM comprising a coherent or partially coherent light source, an interferometric system and a digital image sensor and recorder for storage of acquired images;

providing a fluidic system for inducing a liquid sample stream of the liquid sample through the fluidic system, whereby the fluidic system controls transverse dimensions of the liquid sample stream inside said fluidic system by acoustic focusing and/or hydrodynamic focusing;

inducing the liquid sample stream through the fluidic system;

guiding said objects, lined up multiple objects at a time in three dimensions by controlling the transverse dimensions of the liquid sample stream inside said fluidic system, through an illumination beam of the coherent or partially coherent light source of said DHM;

obtaining three dimensional images by means of said DHM of more than one object of the multiple objects at a time;

performing post-acquisition focusing by flow cytometry on said objects in the liquid sample stream by computer processing of computer processing of stored acquired three-dimensional images; and further observing and/or analyzing said objects with the aid of said DHM, whereby the coherent or partially coherent light source of the DHM comprises a light-emitting diode (LED), an organic light-emitting diode (OLED) or an organic light-emitting field-Effect transistor (OLET).

13. The method according to claim 12, further comprising the step of:

separating said objects from said liquid sample stream according to observed properties of said objects.

14. The method according to claim 12, whereby said objects comprise one or more of biological organisms, cells, cell pigments, DNA- and RNA-strands, chromosomes, proteins, micro-organisms, bacteria, viruses, yeasts, nematodes, enzymes, cytoplasm, membranes, protozoa, or non-biological objects.

15. The method according to claim 12, whereby objects are lined up by acoustic focusing and/or hydrodynamic focusing.

16. The method according to claim 12, wherein one or more of said objects comprises a size larger than a detection limit of the DHM.

17. The flow cytometry system of claim 1, wherein one or more of the objects comprises a size larger than a detection limit of the DHM.

18. The method according to claim 12, wherein said objects comprise impurities or contaminants with respect to the liquid sample being observed, analyzed, and/or separated.

* * * * *

UNITED STATES PATENT AND TRADEMARK OFFICE
CERTIFICATE OF CORRECTION

PATENT NO. : 10,578,541 B2
APPLICATION NO. : 14/378234
DATED : March 3, 2020
INVENTOR(S) : Serge Jooris et al.

It is certified that error appears in the above-identified patent and that said Letters Patent is hereby corrected as shown below:

On the Title Page

Column 1, Item (22), PCT Filed, Line 1, delete "Feb. 3, 2013" and insert --Feb. 13, 2013--.

On Page 3, Column 2, Item (56), under Other Publications, Line 27, delete "Diagnotic" and insert --Diagnostic--.

On Page 3, Column 2, Item (56), under Other Publications, Line 33, delete "epifluorescene" and insert --epifluorescence--.

On Page 3, Column 2, Item (56), under Other Publications, Line 38, delete "Quantative" and insert --Quantitative--.

On Page 3, Column 2, Item (56), under Other Publications, Line 40, delete "retreieved" and insert --retrieved--.

In the Specification

In Column 4, Line 21, delete "laboratoria" and insert --laboratories--.

In Column 13, Line 66, delete "according one" and insert --according to one--.

In Column 14, Line 13, delete "cytoplasma" and insert --cytoplasm--.

In Column 19, Line 25, delete "(209." and insert --(209).--.

Signed and Sealed this
Fourteenth Day of July, 2020

Andrei Iancu
*Director of the United States Patent and Trademark Office*

In the Claims

In Column 20, Line 48, Claim 12, delete "three dimensional" and insert --three-dimensional--.

In Column 20, Line 53, Claim 12, delete "computer processing of" and insert --the--.